(12) United States Patent
Ferranti

(10) Patent No.: US 6,390,818 B2
(45) Date of Patent: May 21, 2002

(54) ERGONOMIC GRIP FOR DENTAL INSTRUMENTS

(76) Inventor: Marann Ferranti, 81 Wheelwright Rd., Hampstead, NH (US) 03841

( * ) Notice: Subject to any disclaimer, the term of this patent is extended or adjusted under 35 U.S.C. 154(b) by 0 days.

(21) Appl. No.: 09/749,213

(22) Filed: Dec. 27, 2000

Related U.S. Application Data

(60) Provisional application No. 60/174,228, filed on Jan. 3, 2000.

(51) Int. Cl.$^7$ ................................................. A61C 3/00
(52) U.S. Cl. ......................................... 433/141; 16/430
(58) Field of Search ................................ 433/141, 142, 433/143; 16/421, 430; 132/26.5, 321; 401/6, 7

(56) References Cited

U.S. PATENT DOCUMENTS

| 5,501,597 A | 3/1996 | Wilson |
| 5,558,452 A | 9/1996 | Oka et al. |
| 5,926,912 A | 7/1999 | Claphan |
| 5,988,909 A | 11/1999 | Luke et al. |

FOREIGN PATENT DOCUMENTS

| DE | 827998 | 1/1952 |
| DE | 4119311 | 12/1991 |

*Primary Examiner*—Todd E. Manahan

(57) ABSTRACT

A pliant elastomeric unitary sleeve is adapted to removably fit the elongate shank of a dental tool which extends beyond a longitudinal end of the shank, whereby to ergonomically enhance a finger grip of the shank in operative manipulation of the dental tool for a dental procedure, said sleeve being characterized by an axially extending generally cylindrical bore sized for circumferentially stressed resilient engagement to said shank, said sleeve being further characterized by an exterior profile, wherein a first peripherally continuous enlargement near one longitudinal end and a second peripherally continuous enlargement near the opposite longitudinal end are longitudinally spaced by a circumferential concavity which is an arcuate contour of revolution about the axis of the sleeve.

14 Claims, 2 Drawing Sheets ic GRIP FOR DENTAL INSTRUMENTS

This application claims the benefit of U.S. Provisional Application No. 60/174,228, filed Jan. 3, 2000, the contents of which are incorporated into this application by reference.

BACKGROUND OF THE INVENTION

Repetitive stress injuries to the hands, wrists, and elbows have become an increasing problem in dental practice. Recent studies show that the prevalence of carpal tunnel syndrome (CTS), and cumulative trauma disorder (CTD), among dental hygienists, may be as high as 54%. *"Carpal Tunnel Syndrome," Am. J. Nursing*, 93:4 (April 1993). There has also been a significant increase in workers' compensation claims by dental clinicians due to disabilities in the hand and wrist areas. Bramson et al., *"Evaluating Dental Office Ergonomics Risk Factors and Hazards," JADA* 129 (February 1998).

BRIEF STATEMENT OF THE INVENTION

It is the primary object of the invention to provide an improved accessory for a dental instrument, so configured and constituted as to enable enhanced efficiency of manipulated use of the instrument, with such comfort to the clinician as to avoid or materially reduce physical distress consequences of the above-noted nature.

The invention in a preferred embodiment achieves this object in an integrally formed sleeve device, removably applicable to the elongate stem or handle portion of a dental examining or operative instrument, such as a scaler or a curette. The device is not only configured for more efficient finger manipulation of the instrument to which it is assembled, but it is also of relatively soft and pliable material for user comfort and for reducing the incidence of hand injuries, such as carpal-tunnel syndrome, tendinitis, fatigue, and undue stress to joints of the hand and/or wrist.

BRIEF DESCRIPTION OF THE DRAWINGS

Preferred embodiments of the invention will be described in detail in conjunction with the accompanying drawings, in which.

DETAILED DESCRIPTION

Figure 1:
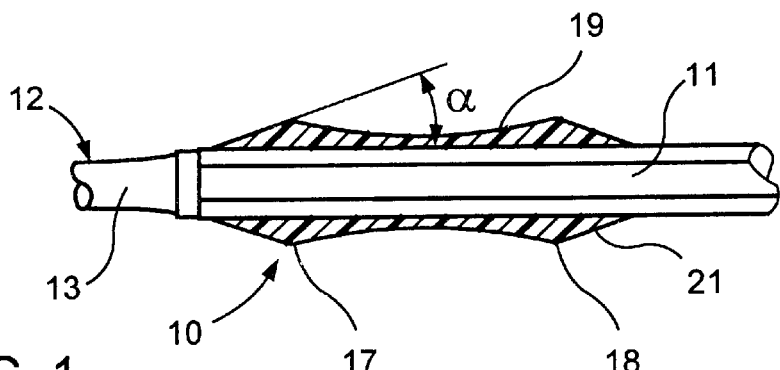
FIG. 1 is a fragmentary side view in elevation of a tool-mounting end of a dental instrument, together with the adjacent handle portion of the instrument, to which an ergonomic-grip device of the invention is shown assembled and in longitudinal section.
Figure 2:
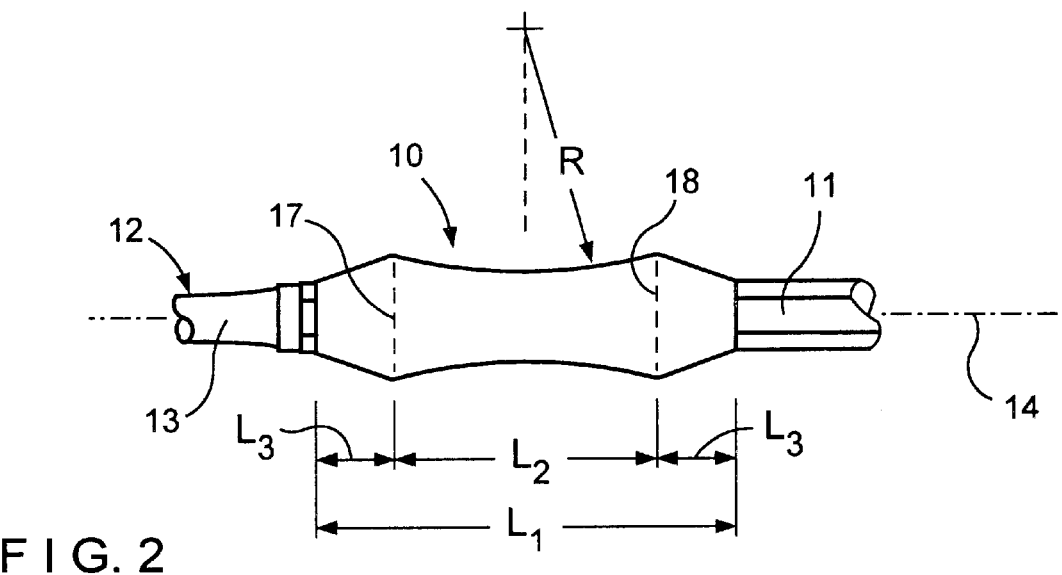
FIG. 2 is a view similar to FIG. 1, wherein the ergonomic-grip device is also in side elevation.

In FIGS. 1 and 2, a preferred embodiment of the invention is shown in the form of an elongate sleeve 10 of elastomeric material having removable slip-fit engagement to one longitudinal end of the handle or shank portion 11 of a dental instrument. In the fragmentary showing of FIGS. 1 and 2, the left-end (i.e., the tool-supporting end) 12 of the shank 11 is reduced at 13 and will be understood to be integrally formed with a dental-tool configuration such as that of a scaler or a curette; and the projecting right-end of the shank 11 will be understood to extend along its central axis 14 for a length suited to operation of the instrument. The right-end formation is not shown but will be understood also to be formed with a reduced section (as at 13) with an integrally formed but different dental-tool configuration; and another elongate sleeve (as at 10) will be understood to have been assembled to the shank or handle 11, adjacent to the right-end tool formation and in end-for-end symmetry with sleeve 10 at the left end. Alternatively, the left-end tool 12 and its handle-connecting end 13 may be the single tool of the instrument, in which case the right-end extension of shank 11 may terminate without a second tool formation.

It is noted that dental instruments of the character indicated are formed to standardized handle cross-sections, which may be of cylindrical or polygonal section. Thus, for example, a "size-2" instrument conforms either to a cylindrical shank of ¼-inch diameter, or to a hexagonal section, wherein the "flat-to-flat" measurement is of so-called "¼-inch diameter". The perimeter of the "hexagonal ¼-inch diameter" instrument handle is thus slightly greater than the circumference of a ¼-inch diameter cylindrical handle. But for purposes of the invention, the same basic "size-2" sleeve 10 will serve for fit to either a hexagonal or a cylindrical handle section, because the bore of the sleeve is selected for slight interference-fit accommodation to the shank section.

Figure 3:
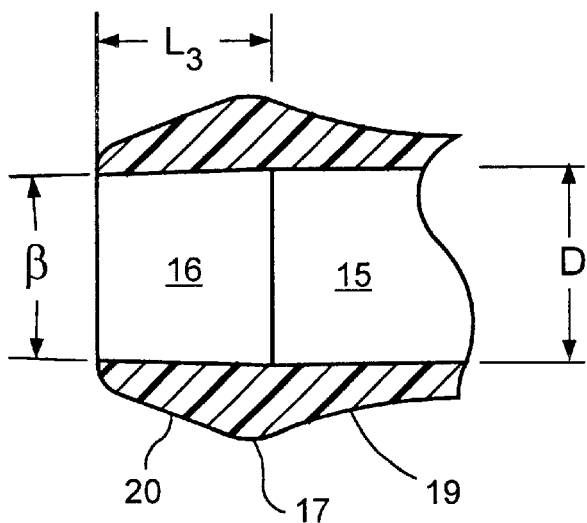
FIG. 3 is an enlarged longitudinal section at one end of the device of FIGS. 1 and 2, to permit identification of an internal feature.

More specifically, and with reference to FIG. 3, the elongate central portion 15 of the bore of the sleeve has only slight interference-fit to the shank section 11, but the longitudinal left and right ends (16) of the bore are convergent in the respective longitudinally outward directions, the angle of convergence being designated β in FIG. 3. In FIG. 3, a single line is shown, marking the location of change from cylindrical portion 15, to the left longitudinally outward convergent portion 16.

The sleeve device 10 importantly features an external contour, wherein a first peripherally continuous enlargement 17 near one longitudinal end of the sleeve 11 is longitudinally spaced from a second peripherally continuous enlargement 18 near the opposite longitudinal end of the sleeve 11. The longitudinal space $L_2$ between enlargements 17, 18 is suitably of arcuate contour to define a circumferentially continuous concavity 19 of radius R, the arcuate contour being of revolution about the central axis 14. A minimum thickness T is thus defined at the longitudinal mid-section of sleeve 11.

The preferred external contour of sleeve 11 is defined by external left-end and right-end conical formations 20, 21 which will be seen to provide longitudinally distributed leftward or rightward referencing for a thumb-and-finger grasp of the dental instrument via the arcuate finger-grasp concavity 19. Specifically, the left-end conical formation 20 converges over the span $L_3$ at an angle α greater than the convergence angle β of the bore taper 16, and with end-for-end symmetry, the right-end conical formation 21 will be understood to converge over an equal span $L_3$ at an angle a greater than the convergence angle β of the rightward end 16.

Figure 4:
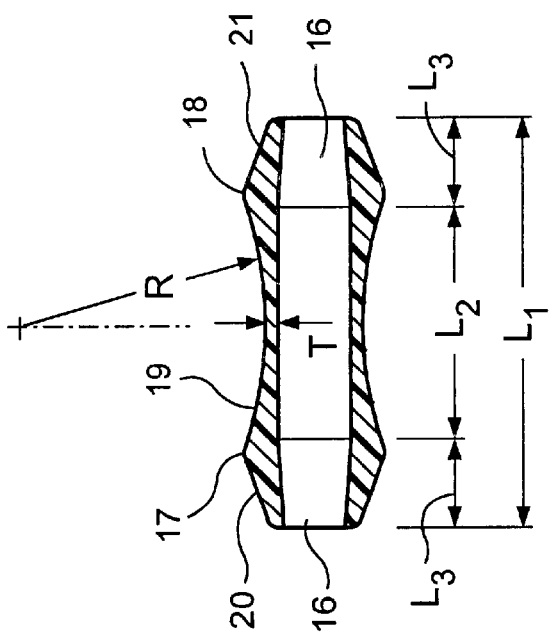
FIG. 4 is a longitudinal sectional view of an ergonomic-grip device of the invention, suitable for application to a first standardized instrument handle-size "diameter"

FIG. 4 serves to illustrate that at least for dental-instrument sizes 2, 4, and 6, for which shank "diameters" are conventionally ¼, 5/16, and 7/16 of an inch, the overall length $L_1$ of a sleeve 11 of the invention can remain substantially the same, and the mid-span diameter D may be substantially equal to the conventional shank "diameter" that applies for the particular tool size (e.g., size 2, or size 4, or size 6). The bore-end convergent angles (β) may be the same for all sizes, except that of course the nominal bore diameter is the principal variable, from one to another size category. Also, the external contouring may remain essentially the same from one size to another; thus, in the larger size of FIG. 5, the shaded upper and lower half-sections may be in general if not exact conformity with the upper and lower half sections of the smaller size of FIG. 4. Contour designations at 17, 18, 19, 20, 21, in FIG. 4 are thus designated by the same numbers, but with primed notation (17', 18', 19', 20', 21') in FIG. 5.

Figure 6:
FIG. 6 is a fragmentary schematic diagram to illustrate a preferred surface feature of a finger-engageable portion of the ergonomic grip device of the invention.

Finally, the schematic showing of FIG. 6 will be understood to suggest preference for a herringbone or other pattern of irregularities in the otherwise smooth contour of the finger-engageable surface, which may provide an optional finger-friction engageability to apply finger-torqued rotary adjustment for selective tool orientation about axis 14, as may be preferred by certain clinicians.

The preferred embodiments that have been described can be seen to have afforded a 40% to 50% increase in grip potential, for a given dental-instrument size category, in each case due to the larger effective diameter of the ergonomic grip device. A dentist's or dental hygienist's clinical career can thereby be extended by years. The ergonomic grip device offers other advantages over standard dental instruments, such as better comfort during procedures, ease of application, translucency to ensure freedom from debris contamination; and color-coding for easy instrument-matching. The ergonomic grip device is designed for autoclaving (high-temperature sterilization), so it does not have to be removed from instruments after every procedure.

Another advantage of the ergonomic grip device is that it is removable yet securely stable on a clinician's dental instrument of choice. There are a few other dental instruments on the market which have permanently integrated, ergonomic handles, but the clinician who chooses such other instrument is restricted to the particular quality and design characteristics of that entire instrument, including the functional component, the tool blade or tip. With the ergonomic grip device, the clinician can enjoy increased ergonomics, still using his or her instruments of choice.

The clinician gains greater control of the dental instrument, with the stable grasp, because the thumb can be used to roll the instrument against the middle and index fingers in precise degrees to adapt the blade to the slightest changes in tooth contour. Pattison & Pattison "Periodontal Instrumentation," p. 152 (Reston, Va., Prentice-Hall) (1979). The ergonomic grip device achieves this optimum type of grip by allowing the user to secure the maximum desired "modified pen grasp." Id. This improves performance with the least amount of effort or stress to the vulnerable joints, muscles, and tendons of the clinician's hands.

To use the ergonomic grip device, the dental clinician, i.e., the dentist, dental hygienist, or dental assistant slips the ergonomic grip device onto the handle of the dental instrument. The ergonomic grip device increases the diameter of the existing instrument to obtain and maintain a more secure grasp throughout a procedure, with less exertion. The alternating "V" pattern (FIG. 6) uniformly impressed throughout the grip area enables unlimited finger-controlled rotation while still maintaining a secure grasp. The slight depression in the mid-section of the ergonomic grip device is designed to help comfortably position the clinician's fingers in the "modified pen grasp," important for exerting the pressure forces necessary to remove calculus when using a curette to scale teeth. According to one study, scaling accounts for 50% of the dental hygienist's work time during an appointment. Bramson, Smith Scot et al. "*Evaluating Dental Office Ergonomic Risk Factors and Hazards,*" *JADA* V. 129, p. 180 (February 1998).

Figure 5:
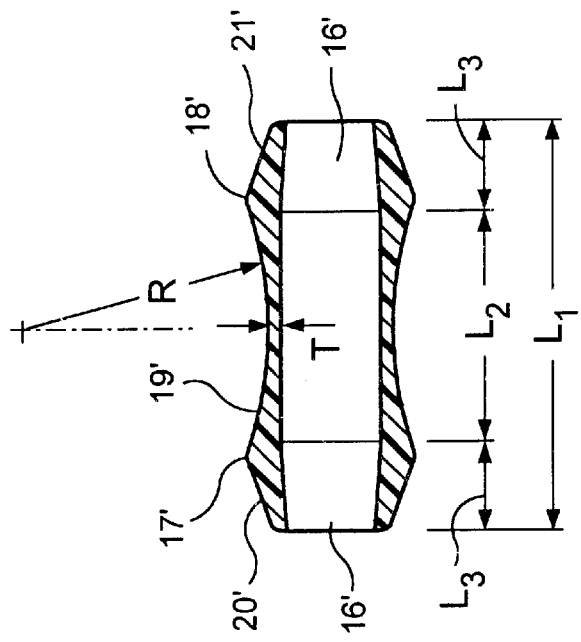
FIG. 5 is a view similar to FIG. 4, for a second and larger standard-size instrument "diameter"

The described design of the ergonomic grip device can also be adapted to restorative instruments used by the dentist. The ergonomic grip device adapts to size-2 handle instruments, which are of 0.25 inches (or 6.5 mm) "diameter", and other sizes of handle instruments; and FIG. 5 shows that a closely analogous version of the ergonomic grip device can be adapted to an instrument having a larger-size handle, to achieve the same benefits with the larger diameter.

The ends of the ergonomic grip device taper down toward the working ends of the instrument, so that the middle finger placed on the shank of an involved curette is in position to maximize tactile sense, precision, and controlled pressure. The device is ergonomically designed to reduce or help prevent work-related ergonomic disorders to the hand by altering a major factor, i.e., instrument grip and pressure. This is decisive in current theory of development of these disorders. By reducing required gripping effort, one relieves stress and fatigue, and obtains the desired results, with less pressure.

The ergonomic grip device is made of soft, semi-transparent or translucent (40–75 A durometer) medical grade silicone; and to date a 45 A durometer for a size-2 instrument has proved very satisfactory. The silicone can be a two-part thermoset resin capable of resisting high temperatures associated with autoclaving (sterilizing), and it is the presently preferred material of the device.

Typical dimensions and durometer number may be various, depending on user preferences, generally, it may be said that convergent ends 16 of the bore are of convergent taper angle β which is suitably 3 degrees, over the range $L_3$, to enhance the force of interference fit of sleeve ends to the section of handle 11. The span $L_2$ of the concave finger-engageable formation 19 is suitably in the range 0.85 to 0.95 inch, being preferably 0.875 inch. The outer contour radius R of the finger-engageable surface 18 is suitably in the range 1.10 to 1.35 inch, and preferably 1.125 inch. The outer convergent end surfaces slope at angle α to the axis 14, in the range 15 to 25 degrees, and preferably 20 degrees. And the minimum thickness T is in the range 0.03 to 0.04 inch, whatever the unstressed instrument "size", over the size range 2 to 6; stated in other words, the minimum radial thickness T is suitably in the order of ¼ to ⅓ of the sectional thickness at each of the crests 17, 18.

It is appropriate to observe a rationale for the reduction in personal stress difficulties when using a dental instrument equipped as described with a sleeve device 10 of the invention, assembled at both of its ends to a tool-mounting end of handle 11, in which case both ends have enhanced stress of handle engagement, by reason of the included angle β of convergent taper (16). For example, the use of a scaler or a curette calls for a "pulling" or a "pushing" effort by the user, to remove a calculus development from a side of a tooth. In either event, the fingers engaged at concave surface 19 will necessarily apply their effort via shared vector components of force—namely, (i) radially opposed squeeze forces to surface 19, and (ii) a longitudinal "pulling" or "pushing" force (as the directional case may be) to the applicable shoulder defined near one of the crests 17, 18, it being noted that the body section of the sleeve at the convergent-end portions 20, 21 are well suited to receive the resultant of these force components and to longitudinally distribute the resultant force by way of enhanced frictional engagement of a bore end 16 to handle 11. Thus, for a "pulling" effort of scale removal, the resultant force development is taken on the concave wall-surface region adjacent crest 18; and for a "pushing" effort, the resulting force development is taken on the concave wall-surface region adjacent crest 17. And for each of these cases of "pulling" or "pushing" action, the median or effective radius of finger-engagement to sleeve 10 is between a crest "height" and the minimum radius of concave surface 19. Thus, finger involvement in instrument action is always at a materially greater radius and via a much more comfortable distribution of compliant engagement to the sleeve-equipped instrument, than would be the case of finger action applied solely to the instrument handle.

While this invention has been particularly shown and described with references to preferred embodiments thereof, it will be understood by those skilled in the art that various changes in form and details may be made therein without departing from the scope of the invention. The entire teachings of each cited reference or article are incorporated herein by reference.

What is claimed is:

1. A pliant elastomeric unitary sleeve adapted to removably fit the elongate shank of a dental tool which extends beyond a longitudinal end of the shank, whereby to ergonomically enhance a finger grip of the shank in operative manipulation of the dental tool for a dental procedure, said sleeve being characterized (a) by an axially extending generally cylindrical bore sized for circumferentially stressed resilient engagement to said shank, and (b) by end-for-end symmetry with respect to the longitudinal mid-point of the sleeve, said sleeve being further characterized by an exterior profile, wherein a first peripherally continuous enlargement near one longitudinal end and a second peripherally continuous enlargement near the opposite longitudinal end are longitudinally spaced by a single circumferential concavity which is an arcuate contour of revolution about the axis of the sleeve and wherein each of the respective longitudinal ends of the exterior profile comprises a convergent substantially frusto-conical taper longitudinally beyond each of the peripherally continuous enlargements.

2. The sleeve of claim 1, in which the elastomeric material of said sleeve is a medical grade silicone.

3. The sleeve of claim 1, in which the material of said sleeve is relatively soft, of durometer in the range 40 to 100 A.

4. The sleeve of claim 1, in which the material of said sleeve is a two-part thermoset resin capable of resisting high temperatures associated with autoclaving.

5. The sleeve of claim 1, in which the minimum radial thickness of said sleeve between said peripherally continuous enlargements is in the range of 25 to 50 percent of the maximum radial thickness at said peripherally continuous enlargements.

6. The sleeve of claim 1, in which the maximum radial thickness at each of said peripherally continuous enlargements is in the range of 80 to 120 percent of the unstressed radius of the bore of said sleeve.

7. The sleeve of claim 1, in which the surface of said circumferential concavity is characterized by a distributed pattern of surface irregularities for finger-engageable friction enhancement.

8. The sleeve of claim 7, in which said pattern is in the nature of a herringbone pattern, wherein clusters of parallel ribs at a first acute angle of divergence are in alternating distribution with clusters of a second and opposite angle of divergence from the axial direction.

9. The sleeve of claim 1, in which the bore of the sleeve has a nominal cylindrical diameter at least in the longitudinal span between said first and second peripherally continuous enlargements.

10. The sleeve of claim 1, in which said exterior frusto-conical tapers converge at an angle in the range of 15 to 25 degrees with respect to the longitudinal axis of the sleeve.

11. The sleeve of claim 10, in which the convergent angle of said frusto-conical tapers is approximately 20 degrees.

12. The sleeve of claim 1, in which in the longitudinal end regions of said convergent frusto-conical tapers, the corresponding longitudinal end regions of the bore are also convergent in the longitudinally outward direction from said generally cylindrical bore.

13. The sleeve of claim 12, in which the convergent angle of the longitudinal ends of said bores is substantially 3 degrees.

14. The sleeve of claim 1, in which the first peripherally continuous enlargement is a first circumferentially continuous crest defined substantially by a first intersection of one of said frusto-conical tapers with said circumferential concavity, and in which the second peripherally continuous enlargement is a second circumferentially continuous crest defined substantially by a second intersection of the other of said frusto-conical tapers with said circumferential concavity.

* * * * *